(12) United States Patent
Shealy

(10) Patent No.: US 6,950,700 B2
(45) Date of Patent: Sep. 27, 2005

(54) ELECTRICAL STIMULATION TO INCREASE CALCITONIN LEVELS

(76) Inventor: C. Norman Shealy, Rte. 1, Box 216, Fair Grove, MO (US) 65648

( * ) Notice: Subject to any disclaimer, the term of this patent is extended or adjusted under 35 U.S.C. 154(b) by 504 days.

(21) Appl. No.: 10/154,411

(22) Filed: May 23, 2002

(65) Prior Publication Data

US 2003/0220669 A1 Nov. 27, 2003

(51) Int. Cl.[7] .................................................. A61N 1/32
(52) U.S. Cl. ............................ 607/2; 128/903; 607/68
(58) Field of Search .......................... 607/1, 2, 68, 115, 607/144, 148–149, 154; 128/907

(56) References Cited

U.S. PATENT DOCUMENTS

| | | | |
|---|---|---|---|
| 5,109,847 A | 5/1992 | Liss et al. | 607/46 |
| 5,609,617 A | 3/1997 | Shealy et al. | 607/68 |
| 6,023,642 A | 2/2000 | Shealy et al. | 607/74 |
| 6,233,489 B1 | 5/2001 | Shealy et al. | 607/68 |

Primary Examiner—Carl Layno
(74) Attorney, Agent, or Firm—Foley & Lardner LLP

(57) ABSTRACT

The endogenous enhancement of calcitonin in a human being has the ability to act as an analgesic and to treat osteoporosis, for example. Exogenous administration of calcitonin has disadvantages given its expense and the possible triggering of a hypersensitivity reaction and other side effects. The present invention provides the benefits of enhanced calcitonin through electrical stimulation that increases endogenous calcitonin levels without the need for exogenous administration of calcitonin.

13 Claims, 5 Drawing Sheets

CARRIER FREQUENCY
15,000 hz MONOPOLAR

1st MODULATOR
15 hz

2nd MODULATOR
500 hz

TYPICAL COMBINED
WAVEFORM (MONOPOLAR)

TYPICAL COMBINED
WAVEFORM (BIPOLAR)

ELECTRICAL STIMULATION TO INCREASE CALCITONIN LEVELS

FIELD OF THE INVENTION

This invention pertains to a method for enhancing calcitonin levels in human beings without exogenous administration of calcitonin.

BACKGROUND OF THE INVENTION

Calcitonin was discovered in 1961 and has been widely used clinically for the treatment Paget's disease, hypercalcemia, osteoporosis, and the relief of bone pain. Calcitonin is a hormone produced by the thyroid gland and secreted in response to high levels of calcium in the blood. Also known as thyrocalcitonin, it lowers the level of calcium in the blood by inhibiting bone resorption, the dissolution of bony tissue. Calcitonin plays a role in pain relief and has been noted for its analgesic effects in bone metastases of primitive cancer and phantom limb pain. It can also enhance or produce recalcification, and is the subject of studies for treatment of peptic ulcers. Though a wide range of pharmacological effects have been attributed to calcitonin, discussion of calcitonin is generally associated with its effectiveness in treating pain and osteoporosis.

Copp reported discovering in addition to parathyroid hormone (PTH), which plays a key role in controlling hypocalcemia by stimulating osteolysis, a second calcium-regulating hormone, calcitonin. Copp found that hypercalcemia and lowered plasma calcium, by inhibiting osteolysis, released calcitonin. Copp was involved in the isolation of salmon calcitonin, which is the form most widely used in therapy because of its high potency. In addition to inhibiting bone resorption, salmon calcitonin is a powerful analgesic agent with a potency in certain circumstances which is 30 to 50 times that of morphine. It is widely used clinically for the treatment of Paget's disease, hypercalcemia, osteoporosis, and relief of bone pain. World sales in 1992 exceeded U.S. $900 million, of which 85% was for osteoporosis. Copp, D. H., "Calcitonin: discovery, development, and clinical application," Clin. Invest. Med., Vol. 17(3), pp. 268–77 (1994).

Osteoporosis is the thinning of bones with reduction in bone mass due to depletion of calcium and bone protein. Osteoporosis predisposes a person to fractures, which are often slow to heal and heal poorly. It is more common in older adults, particularly post-menopausal women, in patients on steroids, and in those who take steroidal drugs. Unchecked, osteoporosis can lead to changes in posture, physical abnormality (particularly in the form of a hunched back known colloquially as "Dowager's Hump"), and decreased mobility. The Food and Drug Administration ("FDA") has announced approval of calcitonin salmon nasal spray for the treatment of osteoporosis. Prior to this approval, only injectable calcitonin salmon and estrogen had been approved to treat or prevent osteoporosis. The FDA reported two randomized clinical trials that demonstrated the daily use of calcitonin nasal spray increases bone mass in the spine. The FDA warns, however, that patients using the nasal spray should have periodic nasal examinations for ulceration or irritation. The most common adverse events reported during clinical trials included rhinitis (inflammation of the membranes in the nose), nosebleeds, and sinusitis (inflammation of the sinus cavity). The FDA emphasized that women on drug therapy for osteoporosis should take daily supplements of calcium and vitamin D. This regimen, along with exercise, has been shown to help prevent the loss of bone mass. Calcitonin salmon nasal spray is manufactured by Sandoz Pharmaceuticals Corp. of East Hanover, N.J., and is marketed under the trade name Miacalcin Nasal Spray. See "FDA Approves New Drug Therapy for Osteoporosis" (1995), available at http://www.fda.gov/bbs/topics/ANSWERS/ANS00677.html.

The effect of space travel on calcitonin levels has been the subject of studies using rats flown on an 18-day shuttle flight. Upon landing, reduced calcitonin levels in the flight animals suggested that space flight disrupts calcium metabolism in animals. It is expected then that extended space flight will require a method of enhancing calcitonin in the bodies of the crew. Hatton, D. C., et al., "Calcium metabolism and cardiovascular function after spaceflight," J. Appl. Physiol., Vol. 92(1), pp. 3–12 (2002).

It has been reported that salmon calcitonin administered for 14 days was more effective than indomethacin in preventing heterotopic ossification. Gunal, I., et al., "Prevention of heterotopic ossification after total hip replacement: a prospective comparison of indomethacin and salmon calcitonin in 60 patients," Acta. Orthop. Scand., Vol. 72(5), pp. 467–9 (2001). Siamopoulou, reported possible beneficial effects of intranasal calcitonin on bone resorption and pain relief in juvenile idiopathic arthritis. Siamopoulou, A., et al., "Effects of intranasal salmon calcitonin in juvenile idiopathic arthritis: an observational study," Calcif. Tissue Int., Vol. 69(1), pp. 25–30 (2001).

Calcitonin has been widely reported as effective in preventing pain in a variety of circumstances. Lyritis, et al., studied the analgesic efficacy of calcitonin suppositories in comparison with bed rest and paracetamol tablets on 40 patients who had recently suffered a non-traumatic osteoporotic vertebral fracture. The test resulted in all calcitonin-treated patients experiencing an overall statistically significant decrease of spinal pain. The pain relief allowed for early mobilization and gradual restoration of the locomotive functions in the calcitonin-treated non-placebo group. Salmon calcitonin suppositories appear to cause a dramatic decrease in spinal pain in patients with recent osteoporotic vertebral fractures and influenced the early mobilization and the gradual restoration of their locomotor functions. Lyritis, G. P., et al., "Analgesic effect of salmon calcitonin suppositories in patients with acute pain due to recent osteoporotic vertebral crush fractures: a prospective double-blind, randomized, placebo-controlled clinical study," Clin. J. Pain., Vol. 15(4), pp. 284–9 (1999).

Calcitonin has also been reported as effective in treating chronic phantom pain. Simanski, et al., reported a decrease in pain intensity after treatment with five cycles of salmon calcitonin infusion on a patient who had suffered a traumatic right-side arm plexus lesion. TENS therapy five times per day showed no analgetic effect. The test was repeated with calcitonin-infusion therapy and after five I.V. cycles, the test was continued with 200 I.U. salmon calcitonin intranasal per day. The initial phantom pain intensity decreased but showed no long-term analgesia. Intravenous salmon calcitonin showed only short-term analgetic effect. Simanski, C., et al., "Therapeutic concept for preventing chronic phantom pain after traumatic brachial plexus lesion," Unfallchirurg, Vol. 104(7), pp. 659–64 (2001) In another study of calcitonin on phantom limb pain, Wall reported that phantom limb pain is a tremendous source of morbidity and suggested that one or two doses of intravenous salmon calcitonin 200 I.U. may be an effective treatment. Wall noted that clinicians should be aware of the rare but severe hypersensitivity reactions that can occur with salmon calcitonin. Internasal calcitonin appears to be similar in efficacy to the parenteral formulation, at least in pain associated with vertebral crush fractures. Wall, G. C., et al., "Calcitonin in phantom limb pain," Ann. Pharmacother, Vol. 33(4), pp. 499–501 (1999).

In a study of calcitonin versus cimetidine or De-Nol in gastric ulcer treatment, it was reported that only the calcitonin group experienced the moderate side effects of headache, nausea, and flushing. Nevertheless, the study suggests that calcitonin may be considered as a valid anti-ulcer drug in the peptic ulcer patients with concomitant rheumatological diseases especially with osteoporosis. Janke, A., et al., "Calcitonin versus cimetidine or De-Nol in gastric ulcer treatment. An endoscopically controlled trial," Dtsch Z. Verdau Stoffwechselkr, Vol. 48(5), pp. 239–43 (1988).

It has been disclosed that treating a patient with electrical stimulation at acupuncture points known as the "Ring of Air," can endogenously increase serum neurotensin levels in living human beings. See U.S. Pat. No. 6,233,489. It has also been disclosed that treating a patient with electrical stimulation at acupuncture points known as the "Ring of Fire" can increase serum dehydroepiandrosterone (DHEA) levels. See U.S. Pat. No. 5,109,847. Until now, however, there has been no known method of endogenously increasing calcitonin levels in a living human being in a manner similar to the "Ring of Air" or "Ring of Fire" electrical stimulation.

SUMMARY OF THE INVENTION

The present invention provides a method for enhancing calcitonin levels in a living human being. Because calcitonin is naturally occurring in the human body, in accordance with the present invention endogenous production of calcitonin may be stimulated without requiring the use of exogenous dietary supplements, suppositories, nasal sprays, injections, I.V.s, or other known delivery methods of pharmaceutical preparations containing calcitonin or calcitonin analogs.

Instead, calcitonin levels in human beings may be raised, in accordance with the present invention, by applying electrical stimulation to specific epidermal points of the individual's body for a period of time, preferably daily. The electrical stimulation is preferably applied to specific locations on the individual's body which correspond to 13 well-known acupuncture points known as the Ring of Earth. The electrical stimulation can be applied to these acupuncture points over a number of weeks to achieve a significant increase in calcitonin levels and a corresponding decrease in pain or bone resorption within the patient. Preferably, electrical stimulation is applied for a minimum period of 2 to 4 weeks.

Electrical stimulation of the acupuncture points on the human body known as the Ring of Earth, in accordance with the present invention, has been shown to be highly efficacious among subjects tested, often elevating calcitonin levels within 45 minutes after a single 30-minute treatment session.

Further objects, features, and advantages of the invention will be apparent from the following detailed description taken in conjunction with the accompanying drawings.

DETAILED DESCRIPTION OF THE PREFERRED EMBODIMENTS

Figure 1:
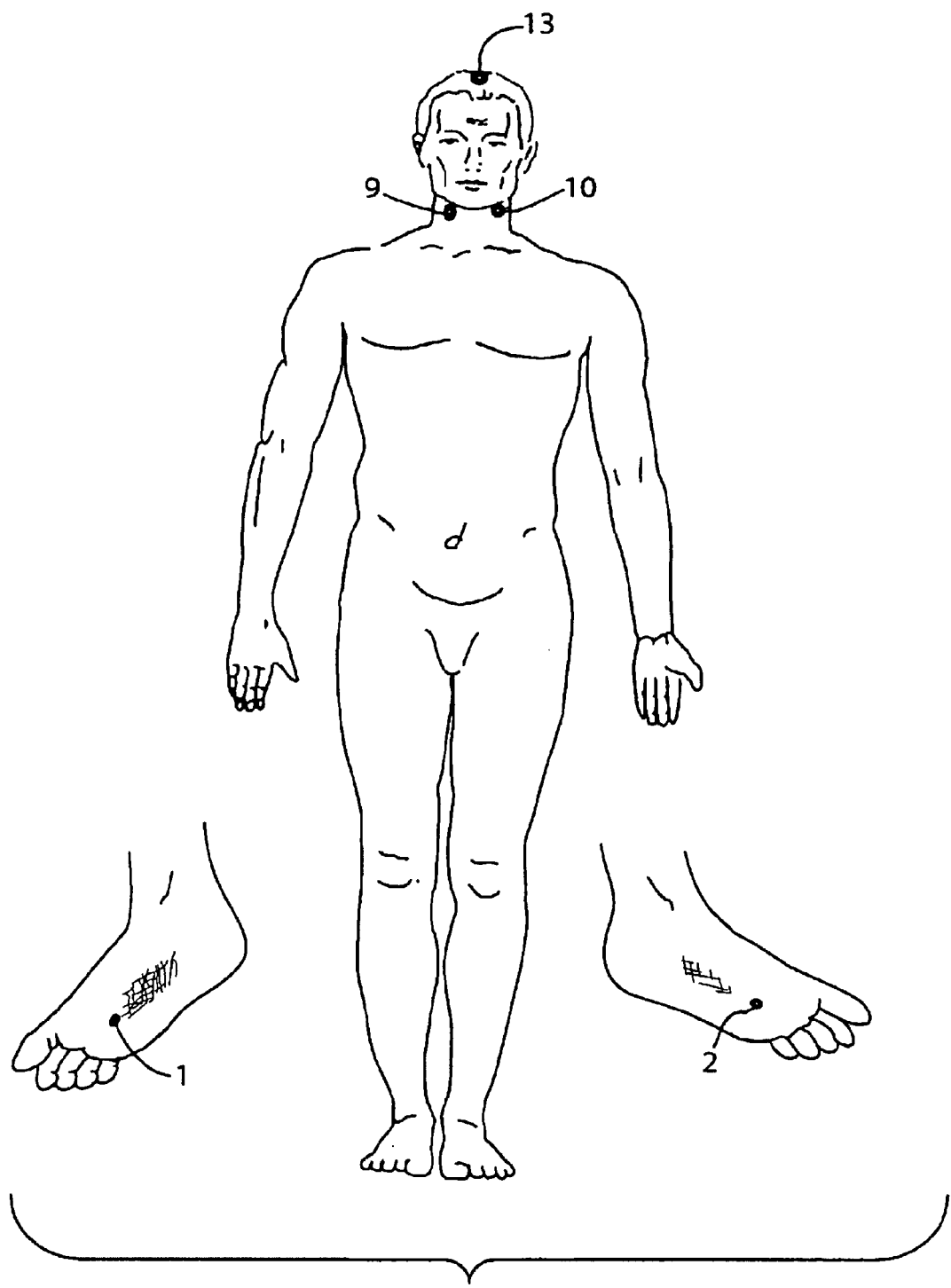
FIG. 1 is a frontal sketch of a human being illustrating five acupuncture points included in the Ring of Earth.

In accordance with the present invention, calcitonin levels may be raised in human beings without the application of exogenous supplements of calcitonin or analogs. Stimulating biosynthesis of calcitonin within the body is advantageous over the heretofore known methods of raising calcitonin levels, which consisted of, for example, salmon calcitonin taken either parenterally, intravenously, subcutaneously, transdermally, or by nasal spray. In clinical studies of exogenous treatments involving their administration, calcitonin, its analogs or equivalents have been associated with undesirable side effects. These side effects include triggering hypersensitivity, rhinitis, sinusitis, ulcerations or irritations in the nasal region, headaches, nausea, and flushing. These and other side effects from the ingestion of calcitonin, and other undesirable consequences involving an exogenous method of calcitonin administration, can be avoided with the method of the present invention. No side effects have been detected from using the present invention to endogenously raise calcitonin levels.

To illustrate performance of the method of the present invention, an apparatus may be used as described in U.S. Pat. No. 5,109,847, the disclosure of which is incorporated by reference. Such apparatus has previously been used to increase serum dehydroepiandrosterone (DHEA) levels in patients by placing electrodes at particular points on an individual's body, specifically, Ring of Fire acupuncture points. See U.S. Pat. No. 5,609,617, the disclosure of which is also incorporated by reference. Such DHEA-enhancing electronic stimulation is preferably performed for 5 minutes at each point on the body where the electrodes are placed and repeated each day for a number of weeks. Such apparatus has also previously been used to stimulate the increase of endogenous neurotensin levels by placing electrodes at particular points on an individual's body, specifically, at the Ring of Air acupuncture points. See U.S. Pat. No. 6,233,489, the disclosure of which is also incorporated by reference.

The method of the present invention is directed to the application of electrical stimulation using the foregoing apparatus to the "Ring of Earth" acupuncture points to stimulate the increase of endogenous calcitonin levels. Calcitonin levels were found to be significantly increased for a majority of subjects within 45 minutes after a single stimulation of 30 minutes using this treatment. In carrying out the invention, a time-varying electrical potential stimulus is applied between the first electrode and the second electrode of the stimulation device. Such electrical stimulus comprises a low-level voltage (typically yielding a current of less than 4 mA) pulse-train of relatively high frequency, i.e., between 12 kHz and 20 kHz, modulated in amplitude by a relatively low-frequency wave in the range of 8 Hz to 20 Hz. The low-frequency wave is preferably non-symmetrical, characterized by a 3:1 duty cycle, being "on" three-quarters and "off" one-quarter of the recurring period. By way of example only, the high-frequency pulses may occur at a 15 kHz rate at about a 4.0 mA level, while being subject to a 15 Hz modulation with a 3:1 duty factor.

Figure 3A:
FIG. 3 are representations of stimulation waveforms that may be utilized in the present invention.
Figure 3B:
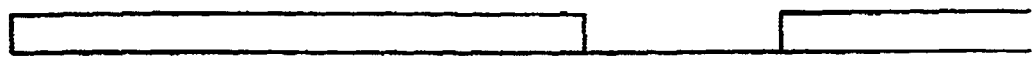
Figure 3C:
Figure 3D:

FIGS. 3A through 3E present the various components of the stimulus waveform in accordance with the invention. More particularly, FIG. 3A is a graphical representation of a carrier frequency signal for one specific time segment. In this example, the carrier frequency is 15 kHz with a duty cycle of 50%. FIG. 3B presents the first modulation to the carrier frequency. In this example, the first modulation has a frequency of 15 Hz in a duty cycle of 0.75. The second modulation is depicted in FIG. 3C. The second modulation has a frequency of 500 Hz and a 50% duty cycle. The waveform of the carrier frequency signal modulated by the signals of FIGS. 3B and 3C is shown in FIG. 3D (in simplified form) and contains 25 bursts of 15 pulses for each burst. The period for each burst is 2 ms and the period for each pulse is 66.7 $\mu$s. For each, the burst and the pulse, the duty cycle is 50% on time.

A cycle for the combined waveform will thus consist of 50 ms "on" time in which the pulses for that frequency combination are generated, and then an "off" time of 16.7 ms.

The complex waveforms of the present invention may be generated with sinusoidal, saw-tooth, hyperbolic, or other wave shapes; for clarity, the waveforms presented in FIG. 3, and further discussed below, have been exemplified by a simple square wave.

Figure 3E:
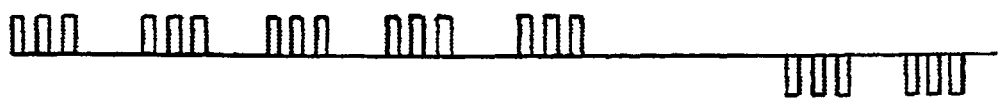

In FIG. 3E, an example of a complex waveform, according to the present invention, is provided wherein the polarity of the output is switched from positive to negative on a periodic basis, e.g., every 67 ms. This is contrasted with the waveform of FIG. 3D in which the polarity remains positive throughout the cycle; the pulsed DC waveform of FIG. 3D is considered a monopolar output while the output waveform depicted in FIG. 3E is considered bipolar.

For purposes of rough approximation, the energy dissipation in using an electrical stimulator according to the present invention is represented by the area under the pulses depicted in FIG. 3B. It can, therefore, be recognized that adding the second modulation, having a 50% duty cycle, results in a 50% decrease in power dissipation.

The stimulation circuit may provide any of the following exemplary frequency combinations (but is not limited to these):

1. 15 Hz, 500 Hz, 15,000 Hz-monopolar;
2. 15 Hz, 500 Hz, 15,000 Hz-bipolar (7.5 Hz);
3. 15 Hz, 500 Hz, 60,000 Hz-monopolar; or
4. 15 Hz, 500 Hz, 60,000 Hz-bipolar (7.5 Hz).

Figure 4:
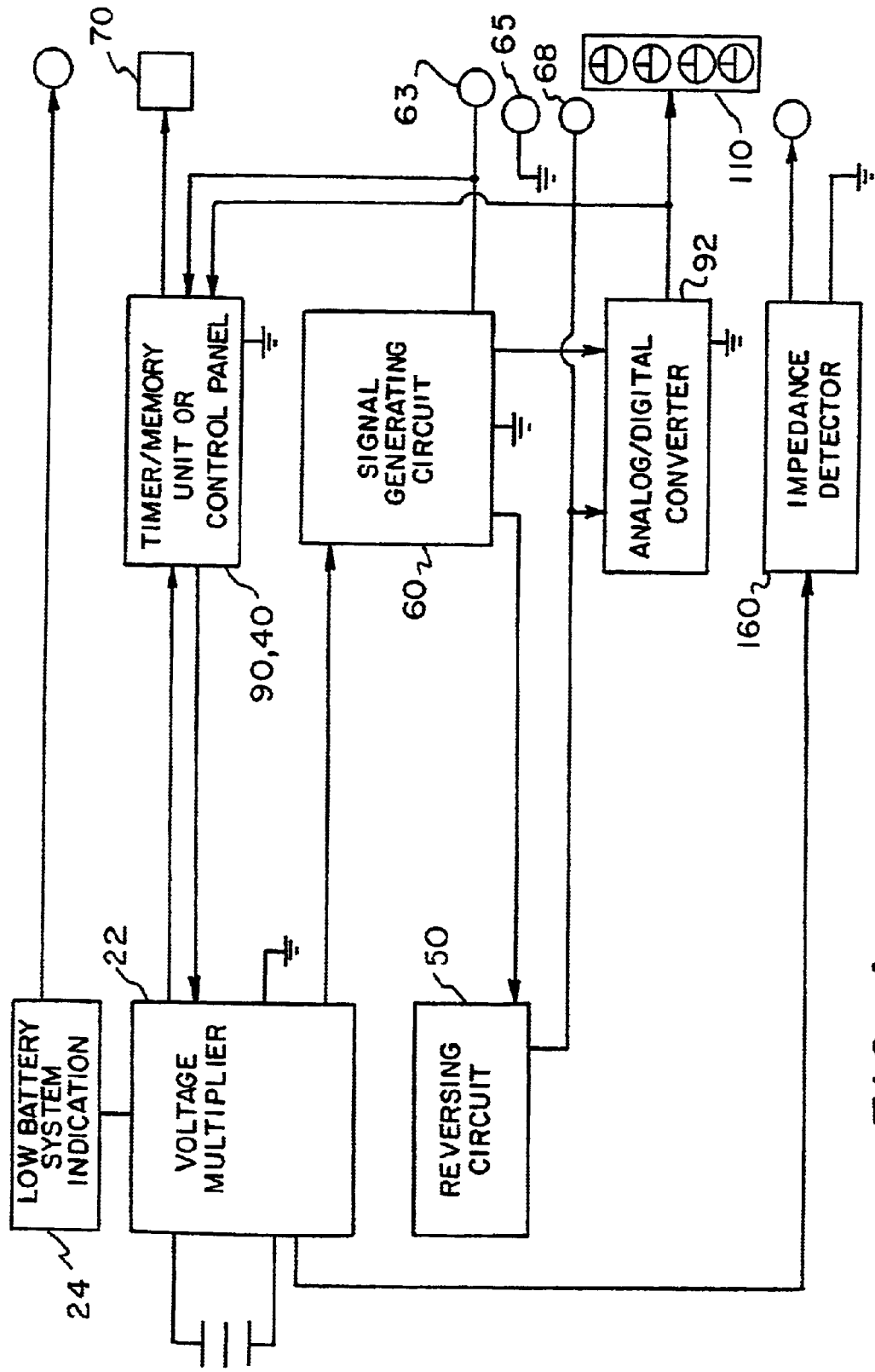
FIG. 4 is a block diagram of an apparatus for generating the stimulation waveforms depicted in FIG. 3.

FIG. 4 shows the functional elements of an electrical stimulator system that may be used in the present invention. The power source to the electrical stimulator will either be a battery having, e.g., a nominal 9 V terminal voltage or some rectified and properly transformed line (AC) power source. The battery provides the basic DC power source for generating the complex waveform. This is channeled and controlled by the voltage multiplier 22. The output of a voltage multiplier 22, which is typically between 27 V to 40 V, is fed to signal-generating circuits 60 which is the oscillating circuit that converts the constant DC output into the complex waveform having the desired characteristics.

The specific constant current and current-limited waveform generated by signal generating circuit 60 is pre-set by entering the various frequency settings for the two modulations and the carrier. This may be entered manually through adjusting the settings on control panel 90. Alternatively, these settings may be stored in digital memory 40 as previously set values. The actual output of this system is regulated by monitor 70 which then provides the system output on a display, via control panel 90, or a memory value for subsequent retrieval from digital memory 40.

The signal generating circuit 60 receives the output voltage from voltage multiplier 22. Within the signal generating circuit 60, the voltage branches off into a carrier frequency and two modulation frequencies. An example of the branching of the waveform is described in FIG. 3.

As shown in FIG. 4, the system supports two separate electrodes for placement on the patient. An electrode terminal 63 represents the positive terminal which receives the signal generated by the signal generating circuit 60. A second electrode terminal 65 is grounded within the circuit. For applying a bipolar stimulation waveform, the stimulation electrodes are connected to electrode terminals 65 and 68. The terminal 68 receives the output from a reversing circuit 50, which acts to flip the signal from the generating circuit 60 pursuant to preset timing constraints.

The following ancillary systems are also preferably present in the circuit. The low battery and system-on indicator 24 monitors the battery output via a voltage multiplier 22, and it generates an alarm signal when battery output voltage drops below a preset limit, for example, 7.0 V. It also shuts the system down if the battery output voltage falls below a preset limit of approximately 6.0 V.

The analog/digital converter 92 converts the signal from the signal generating circuit 60 so that the patient can read it. The analog/digital converter 92 senses the output voltage and converts it to an appropriate signal for the 4-gate integrated circuit which uses the signal to turn on the appropriate sequence of 4 LEDs 110. Finally, the impedance detector 160 is used to determine if the system is being used on a person (as opposed to someone just running the system without attaching it to a person).

Figure 5:
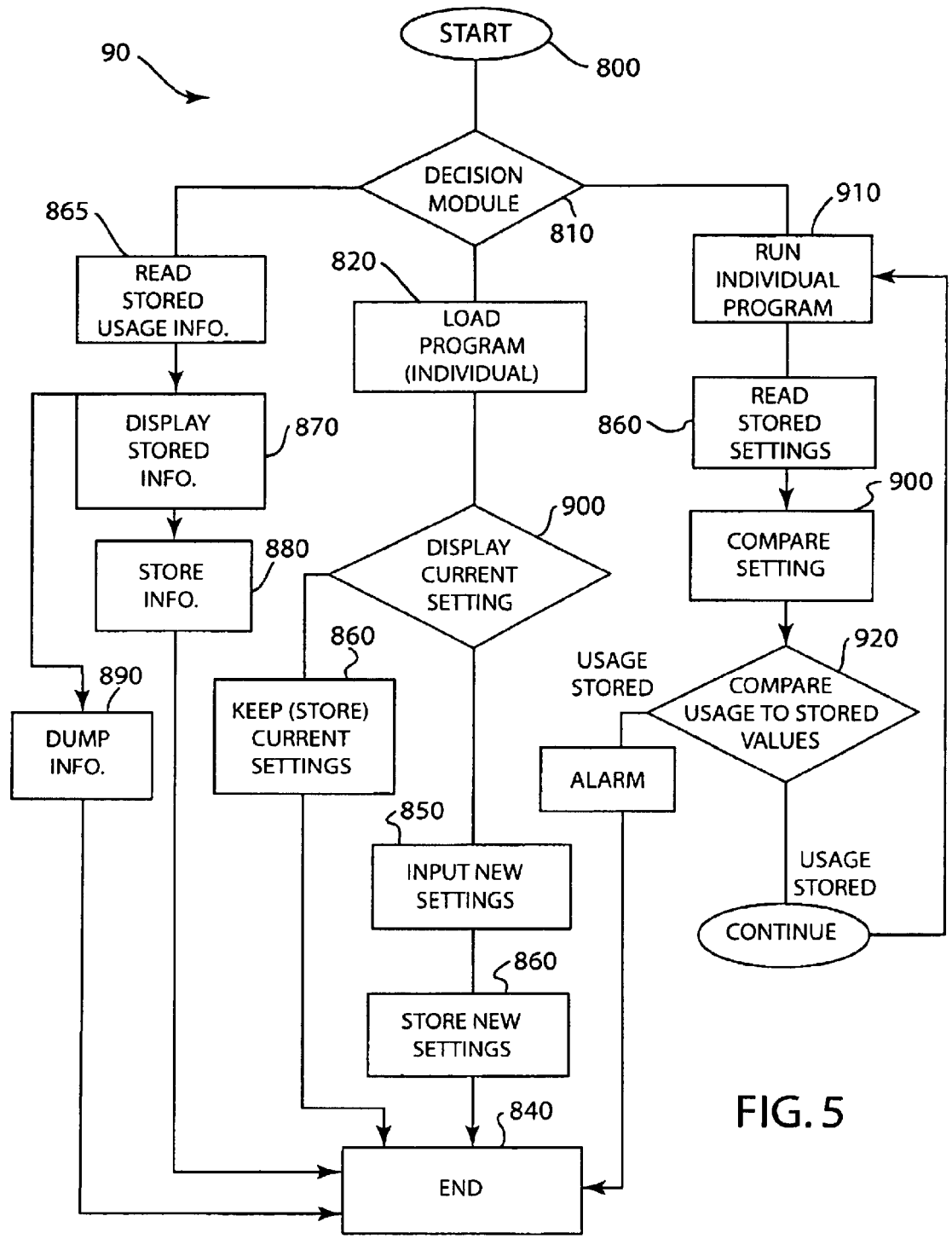
FIG. 5 is a logic flowchart of a data processing program controlling the operation of the apparatus of FIG. 4.

FIG. 5 is a flowchart of the operation of the timer unit 90 which the apparatus will use to monitor usage by the patient. This program will prevent the patient from misusing the electrical stimulator apparatus and will allow the physician to set an individual treatment program and to monitor the patient's compliance to the set program. The timer unit 90 will allow the therapist to set the number of days this system is to be used, the number of times per day the system will be used, and the time duration for each use.

The program 800 starts with an Origination Decision Module 810. The Original Decision Module 810 will give the therapist three choices for use. If the Individualized Program 820 pathway is chosen, the timer unit will load the Individualized Program 820. Then the Individualized Program 820 will begin with a display showing the Current Setting 900 for each of the parameters (i.e., the number of days of use, the number of times per day of use, and the length of time for each use).

Next, the program will ask the therapist whether he or she wants to keep the current settings 855 or input new settings 850. If the therapist wishes to use the same settings as already registered in the program 800, the Individualized Program 820 will Store 860 the values and will End 840. However, if the therapist wishes to change the settings, the program will proceed to the Change Input Values 850 module in which the computer will ask the therapist for the new values for the settings. Then, the computer will Store 860 the new values and will End 840.

Another selection which a therapist may make at the Origination Decision Module 810 is to read the stored information from the patient's system. If the therapist decides to access the Read Stored Results 865 module, the Setting and Use information will be displayed 870 and the therapist will decide whether to store the patient information in the Patient Storage Module 880, or else it will dump the information 890 and it will End 840. A final selection which the therapist may access through the Origination Decision Module 810 is actually to use the system. Selecting this choice will initialize the Run Timed Program 910. The Run Timed Program 910 will read the Stored 860 values, then the program will Check 920 any Stored 860 values against the current run settings 900, which are the values of the Run Timed Program 910 for this usage of the system. If the current running settings 900 for the number of days of use is greater than the Stored 860 values, the program will End 840 without the system being turned on. Next, the Run Timed Program 910 will check the value of the Stored 860 values for the number of uses for a given date and, if the current running settings 900 are greater than the stored 860 values for the number of uses for a day, the system will End 840 for that day, and the system will not be able to be used until the next day. Finally, as the system is being used, a Running Time Clock will be compared to the Run Timed Program 910, and when the current running settings in 900 are greater than the Stored 860 values for the length of time for that session, the system will End 840 for that session, and the system will not be able to be used until the next session.

The LISS Cranial Stimulator (MEDIC Consultants, Inc., 265 Vreeland Avenue, Patterson, N.J.) is a commercially available device which provides an electrical signal equivalent to the corresponding signal described above. The device is the preferred electrical stimulator which produces a high-frequency electrical wave bearing a low-frequency amplitude modulation to a pair of electrodes used in the present invention. The LISS stimulator emits typically 1 to 4 mA at 15,000 pulses per second, which is modulated 15 and 500 times per second. It has been used in well over 20,000 patients with no known complications.

A second exemplary apparatus that has been found to increase calcitonin levels in human beings is the compact transcutaneous electrical nerve stimulator (Shealy TENS) described in U.S. Pat. No. 6,023,642 to Shealy, et al. This exemplary therapeutic device may be conveniently carried or worn by a patient. The output signal of the device includes a broad range of frequency components, extending into the GHz range, that may be provided to a patient via electrodes placed on the patient in appropriate locations. The Shealy TENS and the LISS stimulator have proven capable of activating acupuncture points neurochemically.

Another form of electric stimulation of individuals has been found to increase calcitonin levels in individuals. This stimulation may be applied by use of an apparatus capable of delivering a very high frequency electrical stimulus, e.g., up to 300 GHz at an energy level of up to 1 $\mu$V. This apparatus, referred to as a GigaTENS™ Electrical Stimulator, is used to provide the proper electrical stimulation to the individual to increase calcitonin levels by placing a single electrode from the device on specific points of an individual's body and then applying a very high frequency electrical stimulus, e.g., up to 30 GHz at a power level of $10^{-9}$ W/cm$^2$, and preferably at 52 to 78 GHz at an electrical power of $10^{-9}$ W/cm$^2$, in a sequential manner to a number of specific points on the individual's body.

Figure 2:
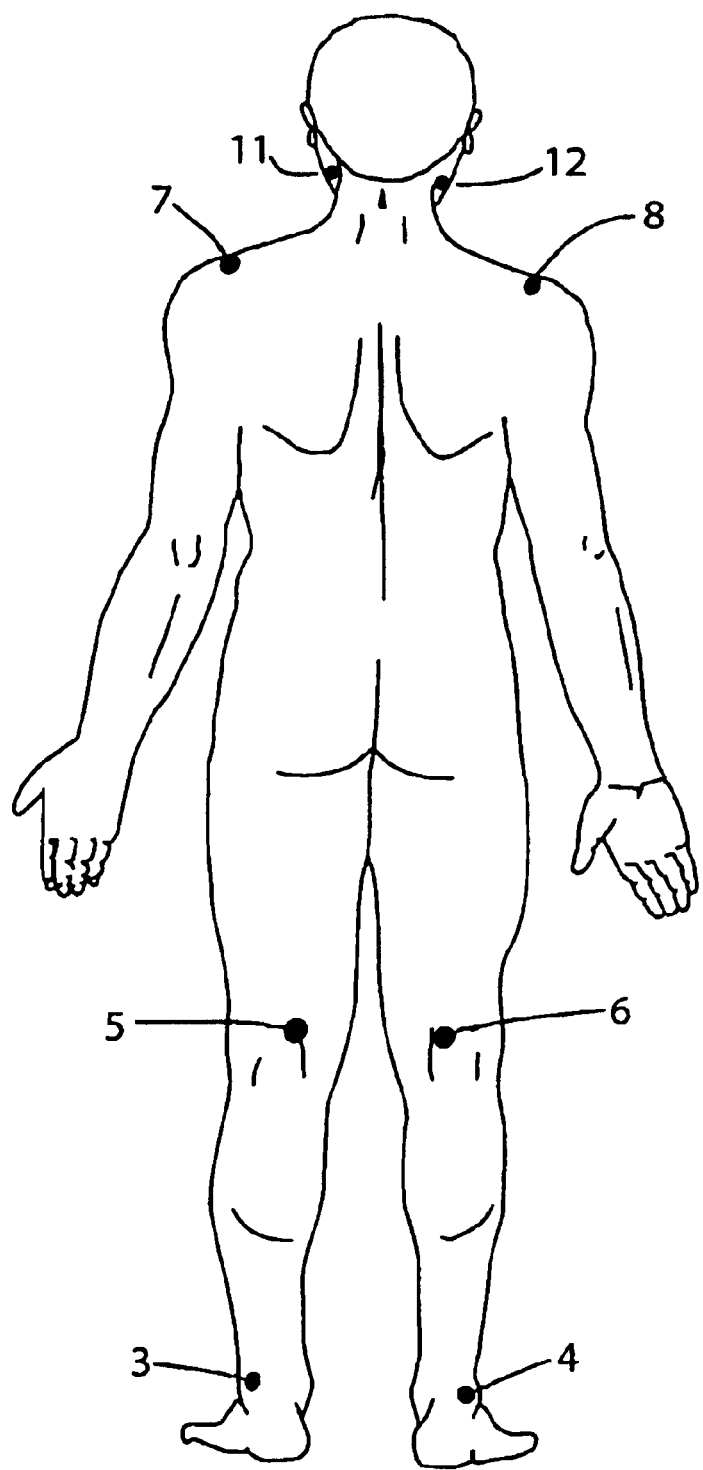
FIG. 2 is a back profile sketch of a human being illustrating eight acupuncture points included in the Ring of Earth.

For the method of the present invention, these specific points on the individual's body correspond to 13 acupuncture points, hereinafter defined as the "Ring of Earth." The Ring of Earth points are located on the body as illustrated in FIGS. 1 and 2, and they correspond to the well-known acupuncture points of K1, B54, B60, LI16, S9, SI17, and GV20, as detailed in Table 1. Generally, positions 1 and 2 are the middle ball of each foot; positions 3 and 4 are the top and outside of the ankle bone; positions 5 and 6 are the inside hollow on the back of the knee; positions 7 and 8 are where the arm meets the shoulder located by the dip behind where the collar bone meets the shoulder; positions 9 and 10 are the top of the Adam's apple and to each side; positions 11 and 12 are behind the angle of the jawbone; and position 13 is the center top of the head. Although these acupuncture points are well known in Chinese acupuncture literature, it has been surprisingly and unexpectedly discovered in accordance with the present invention that this combination of acupuncture points, i.e., the Ring of Earth, can be electrically stimulated to increase calcitonin levels in individuals.

TABLE 1

Ring of Earth Points

| | |
|---|---|
| K1 | In the depression at the junction of anterior and middle third of the sole in a depression between the 2$^{nd}$ and 3$^{rd}$ matatarso-phalangeal joint when the toes are plantar flexed. |
| B54 | Exact midpoint of the popliteal transverse crease. |
| B60 | Between the posterior border of the external malleolus and the medial aspect of tendo calcaneus, at the same level as the tip of the malleolus. |
| LI16 | In the depression between the clavico-acromal extremity and the spine of the scapulae. |
| ST9 | Posterior to the common carotid artery on the anterior border of the M. sternocleidomastoid, lateral to the thyroid cartilage. |
| SI17 | Posterior to the angle of the jaw on the anterior border of M. sternocleidomastoid. |
| GV2O | 7 cun above the posterior hairline, midway on a line connecting apex of both ears. (1 cun = distance between the two creases marking the joints of the distal and middle phalanges of the middle finger.) |

Stimulation of the acupuncture points in accordance with the present invention may be carried out in a variety of sequences. One preferred method of carrying out the method of the present invention includes applying one electrode throughout the procedure at Governing Vessel 20 (GV20). Since the Shealy TENS is a monopolar stimulator, one preferred method is to place the negative electrode at GV20. For the bipolar LISS stimulator, the relative placement of its electrodes is immaterial. By way of example only, the contacts of the opposing electrode can be placed at pairs of acupuncture points beginning with points near the feet and sequentially stimulating points successively approaching the head. However, the present invention is not limited to any particular sequence.

When using the Shealy TENS or the Liss TENS stimulator, a preferred period of treatment at each acupuncture point is about 5 minutes, and the acupuncture points are preferably stimulated in pairs as described above. One electrode is preferably maintained continuously at GV20, and then the electrodes are applied in pairs to six pairs of the Ring of Earth acupuncture points. When stimulating using the GigaTENS™, each acupuncture point is treated individually because the stimulation is applied at a single point through a single electrode. The preferred period of treatment using the GigaTENS™ is about three minutes at each acupuncture point.

The stimulation method in accordance with the present invention was shown to be effective in many cases with a single application. Thus, the treatment appears demonstrably effective with a single stimulation and is foreseeably enhanced by repeated stimulation over longer periods. A preferred long-term treatment regiment could include stimulation in accordance with the present invention, preferable about once per week.

The present invention is further illustrated by the following exemplary research study which is not to be construed as limiting, but merely as an illustration of some preferred features of the invention.

EXAMPLE

As shown in Table 2, 10 adult subjects, 6 females and 4 males, ranging in age from 26 to 72, volunteered for this study. A fasting blood was drawn to measure baseline calcitonin level. The subjects then received electrical stimulation from one of two different TENS devices, the Liss TENS and the Shealy TENS, to the 13 acupuncture points identified as the Ring of Earth. Electrical stimulation was applied in each case between an electrode at GV20 and a pair of electrically connected electrodes placed sequentially at six pairs of points corresponding to K1, B54, B60, LI16, ST9, and SI17. Each pair of points was stimulated with respect to the electrode at GV20 for about 5 minutes for a total of 30 minutes of stimulation. Thirty minutes after conclusion of the stimulation, another blood sample was drawn. No further intervention was made. Serum extracted from the blood sample was frozen and sent overnight to the research laboratory at the University of Pennsylvania at Hershey for analysis. The results are detailed in Table 2.

TABLE 2

Enhancement of Calcitonin Levels via Application of Electrical Stimulator to the Ring of Earth Calcitonin (pg/ml)

| Test Subject | Sex | Age | Baseline | Post Stimulation | Stimulator |
|---|---|---|---|---|---|
| 1 | F | 35 | 3 | 5.4 | LISS |
| 2 | F | 56 | 6.0 | 8.0 | Shealy TENS |
| 3 | F | 42 | <1 | <1 | LISS |
| 4 | F | 42 | <1 | <1 | LISS |
| 5 | F | 72 | <1 | <1 | Shealy TENS |
| 6 | F | 53 | <1 | <1 | LISS |
| 7 | M | 69 | 3.2 | 4.5 | Shealy TENS |
| 8 | M | 62 | 2.7 | 4.1 | Shealy TENS |
| 9 | M | 26 | 5.1 | 7.1 | Shealy TENS |
| 10 | M | 45 | 8.1 | 12.1 | Shealy TENS |

In the research study, the 4 women who had no measurable baseline calcitonin were all post-menopausal, and none of them exhibited any immediate effect from the stimulation. Although one menopausal woman, subject No. 2 in Table 2, exhibited a rather modest effect with the LISS stimulator of less than 10% increase in calcitonin, she experienced a 33% increase in calcitonin level when retested using the Shealy TENS. Among the women who had measurable baseline calcitonin, the stimulation therapy increased calcitonin levels 30% to 80%.

Although this study examined a small number of patients, the increase in calcitonin among those who had measurable calcitonin baseline levels demonstrates the value of this technique. In addition to this research study, at least several dozen patients with chronic pain have benefited significantly from clinical pain management using the stimulation of the Ring of Earth as described by the present invention. For example, one patient with a paraparetic pain syndrome, for whom all previous attempts at pain control had failed, has had his pain well-controlled for 15 months by Ring of Earth stimulation using a Shealy TENS apparatus.

The present invention may be embodied in other specific forms without departing from its spirit or its central characteristics. The described embodiments are to be considered in all respects only as illustrative and not restrictive. The scope of the invention is, therefore, indicated by the following claims, rather than by the foregoing description. All changes which come within the meaning and range of equivalency of the claims are to be embraced within their scope.

What is claimed is:

1. A method of increasing calcitonin levels in an individual comprising the steps of:
    (a) applying electrodes sequentially to at least one selected Ring of Earth acupuncture point of the individual's body; and
    (b) applying a high-frequency of at least 1 kHz electrical stimulus bearing a low-frequency amplitude modulation to the electrodes at each selected acupuncture point repetitively over a period of time sufficient to result in stimulation of endogenous production of calcitonin within the individual.

2. The method of claim 1 wherein the electrical stimulation is applied for a period of time of approximately five minutes at each acupuncture point at least once per day over a period of at least one day.

3. The method of claim 1 wherein the frequency of the high-frequency electrical stimulation is in the range of 12 to 20 kHz, the low-frequency amplitude modulation is in the range of 8 to 20 Hz, and wherein the current applied to the individual by the electrical stimulation does not exceed about 4.0 mA.

4. The method of claim 3 wherein the amplitude of the modulation is non-symmetrical.

5. A method of increasing calcitonin levels in an individual comprising the steps of:
    (a) applying an electrode sequentially to at least one selected Ring of Earth acupuncture point of the individual's body; and
    (b) applying an electrical stimulus have a frequency of 52 to 78 GHz at a power level of about $10^{-9}$ W/cm$^2$ to the electrode at each selected acupuncture point repetitively over a period of time sufficient to result in stimulation of endogenous production of calcitonin within the individual.

6. The method of claim 5 wherein the electrical stimulation is applied for a period of time of approximately three minutes at each acupuncture point.

7. A method of enhancing calcitonin levels in an individual comprising the steps of:
    (a) applying a first electrode sequentially to at least one selected Ring of Earth acupuncture point of the individual's body;
    (b) applying a high-frequency electrical stimulus bearing a low-frequency amplitude modulation to the first electrode at each acupuncture point;
    (c) applying a second electrode sequentially to at least one other selected Ring of Earth acupuncture point of the individual's body;
    (d) applying a high-frequency electrical stimulus to the second electrode at each acupuncture point; and
    (e) repeating steps (a) through (d) repetitively over a period of time sufficient to result in stimulation of endogenous production of calcitonin within the individual.

8. The method of claim 7, wherein steps (a) through (d) are repeated for each Ring of Earth acupuncture point of the individual's body, and the high-frequency electrical stimulus is conducted for at least about five minutes at each Ring of Earth acupuncture point.

9. A method of enhancing calcitonin levels in an individual comprising the steps of:
    (a) applying an electrode sequentially to at least one selected Ring of Earth acupuncture point of an individual's body;

(b) applying a high-frequency electrical stimulus to the electrode at each acupuncture point; and (c) repeating steps (a) through (b) repetitively over a period of time sufficient to result in stimulation of endogenous production of calcitonin within the individual, wherein steps (a) through (b) are repeated daily over a period of at least one day, and wherein the high-frequency electrical stimulus is conducted for a period of about 3 minutes using an electrical stimulator delivering up to 78 GHz at an electrical power up to about $10^{-9}$ W/cm$^2$.

10. A method of enhancing calcitonin levels in an individual comprising the steps of:

(a) applying electrodes, the electrodes attached to an electrical generator, to Ring of Earth acupuncture points sequentially at each of the acupuncture points; and (b) applying an electrical stimulus to the electrodes from the electrical generator, the stimulus having a moderately high-frequency of at least 1 kHz and an electrical amplitude which does not exceed 2 mA, to stimulate endogenous production of calcitonin within the individual.

11. The method of claim 10 wherein the step of applying the electrical stimulus further comprises applying the electrical stimulus for a period of about 5 minutes to the electrodes.

12. A method of enhancing calcitonin levels in an individual comprising the steps of:

(a) applying electrodes sequentially to at least one selected Ring of Earth acupuncture point on an individual's body;

(b) applying an electrical stimulus having a frequency of from about 52 GHz to about 300 GHz sequentially to the electrodes at each of the selected Ring of Earth acupuncture points; and (c) continuing electrical stimulus for approximately three minutes at each point to stimulate endogenous production of calcitonin within the individual.

13. The method of claim 12 wherein the amplitude of the electrical stimulus does not exceed 1 $\mu$V at any one acupuncture point.

* * * * *